(12) United States Patent
Alvarado

(10) Patent No.: US 9,023,342 B2
(45) Date of Patent: May 5, 2015

(54) TISSUE GRAFTING METHOD

(71) Applicant: Carlos A. Alvarado, Ft. Worth, TX (US)

(72) Inventor: Carlos A. Alvarado, Ft. Worth, TX (US)

(73) Assignee: Carlos A. Alvarado, Guatemala (GT)

( * ) Notice: Subject to any disclaimer, the term of this patent is extended or adjusted under 35 U.S.C. 154(b) by 0 days.

(21) Appl. No.: 14/049,264

(22) Filed: Oct. 9, 2013

(65) Prior Publication Data

US 2014/0037595 A1 Feb. 6, 2014

Related U.S. Application Data

(62) Division of application No. 12/452,717, filed on Jan. 19, 2010, now abandoned.

(51) Int. Cl.
| | | |
|---|---|---|
| *A61K 35/12* | (2006.01) | |
| *A61K 35/37* | (2006.01) | |
| *A61K 35/38* | (2006.01) | |
| *A61L 27/36* | (2006.01) | |
| *B65B 55/12* | (2006.01) | |

(52) U.S. Cl.
CPC ............ *A61L 27/3629* (2013.01); *B65B 55/12* (2013.01); *A61L 27/3687* (2013.01); *A61L 27/3691* (2013.01); *A61L 2430/40* (2013.01)

(58) Field of Classification Search
None
See application file for complete search history.

(56) References Cited

U.S. PATENT DOCUMENTS

| | | |
|---|---|---|
| 3,562,820 A | 2/1971 | Braun |
| 4,902,508 A | 2/1990 | Badylak et al. |
| 4,956,178 A | 9/1990 | Badylak et al. |
| 5,300,306 A | 4/1994 | Alvarado et al. |
| 5,554,389 A | 9/1996 | Badylak et al. |
| 5,755,791 A | 5/1998 | Whitson et al. |
| 5,866,414 A | 2/1999 | Badylak et al. |
| 5,885,619 A | 3/1999 | Patel et al. |
| 6,666,892 B2 | 12/2003 | Hiles et al. |
| 6,696,270 B2 | 2/2004 | Badylak et al. |
| 6,890,351 B2 | 5/2005 | Termin et al. |
| 6,893,666 B2 | 5/2005 | Spievak |
| 6,933,326 B1 | 8/2005 | Griffey et al. |
| 7,160,326 B2 | 1/2007 | Ball |
| 7,175,841 B2 | 2/2007 | Badylak et al. |
| 2003/0059405 A1 | 3/2003 | Spievack |
| 2004/0043006 A1 | 3/2004 | Badylak et al. |

*Primary Examiner* — Cherie M Stanfield
*Assistant Examiner* — Paul D. Pyla
(74) *Attorney, Agent, or Firm* — Litman Law Offices, Ltd.

(57) ABSTRACT

The tissue grafting method relates to a tissue graft material, a method of preparing the material, and a method of using the material. The tissue graft material is made from the tunica serosa of the small intestine of a warm-blooded vertebrate, which has been delaminated from the tunica muscularis, tunica submucosa, and the tunica mucosa of the intestinal tissue. The tissue graft material may be perforated by discrete punctures. The tissue graft material is dehydrated by air drying or vacuum drying, sterilized with ethylene oxide, and stored in a hermetically sealed enclosure at room temperature until needed, having an indefinite storage life. When needed, the tissue graft material is rehydrated, cut to match the size of the wound, and applied to the wound. The graft may be overlaid with nylon mesh, or bandaged with an elastic tubular dressing.

8 Claims, No Drawings

TISSUE GRAFTING METHOD

CROSS-REFERENCE TO RELATED APPLICATION

This application is a division of application Ser. No. 12/452,717, filed Jan. 19, 2010, which claims the benefit of PCT/IB2008/053921, filed Sep. 25, 2008, which claims the benefit of U.S. Provisional Patent Application Ser. No. 60/960,376, filed Sep. 27, 2007.

FIELD OF THE INVENTION

The present invention relates to a tissue graft, a method of preparing the tissue graft, and a method of using the tissue graft for the treatment of burns, cuts, or other wounds.

DESCRIPTION OF THE RELATED ART

Wounds that involve injuries to significant areas of human skin are difficult to treat. Covering the wound is an important aspect to successful care, and is often limited by lack of suitable autograft material. As a result, resort is usually made to allografts, often from cadavers. However, often a suitable donor is not at hand due to the requirement for immune system compatibility. This can prove to be a taxing problem, particularly when the patient has extensive burn or wound area requiring skin replacement, or in the case of disasters involving multiple burn victims. When autografts and allografts are not available, xenografts or biologic dressings are used to cover the area until a suitable allograft is available, often using porcine tissue.

Nevertheless, even suitable xenograft material may not be available, as such graft material has a limited storage life. Frequently covering the wound area as quickly as possible is necessary to prevent infection and promote healing. There is a need for a suitable tissue graft material that has an extended or indefinite storage life for use as skin graft material or biologic dressings for burns, cuts, or other wounds requiring a skin graft.

Thus, a tissue grafting method solving the aforementioned problems is desired.

SUMMARY OF THE INVENTION

The tissue grafting method relates to a tissue graft material, a method of preparing the material, and a method of using the material. The tissue graft material is made from the tunica serosa of the small intestine of a warm-blooded vertebrate, which has been delaminated from the tunica muscularis, tunica submucosa, and the tunica mucosa of the intestinal tissue. The tissue graft material may be perforated by discrete punctures. The tissue graft material is dehydrated by air drying or vacuum drying, sterilized with ethylene oxide, and stored in a hermetically sealed enclosure at room temperature until needed, having an indefinite storage life. When needed, the tissue graft material is rehydrated, cut to match the size of the wound, and applied to the wound. The graft may be overlaid with nylon mesh, or bandaged with an elastic tubular dressing.

Previously, the tunica serosa had simply been discarded from xenograft tissues. The present inventor has found, however, that the tunica serosa from the small intestine adheres almost instantaneously to the wound area, remains for a long period without shrinkage or distortion, and when stored as described above, has a long or indefinite storage life. The tissue graft material is particularly well suited for superficial and deep second degree burns (partial thickness burns, erosions, or abrasion by cosmetic peeling.

These and other features of the present invention will become readily apparent upon further review of the following specification.

DETAILED DESCRIPTION OF THE PREFERRED EMBODIMENTS

The present invention is a tissue grafting method that relates to a tissue graft material, a method of preparing the material, and a method of using the material. The tissue graft material is made from the tunica serosa of the small intestine of a warm-blooded vertebrate, which has been delaminated from the tunica muscularis, tunica submucosa, and the tunica mucosa of the intestinal tissue. The tissue graft material may be perforated by discrete punctures. The tissue graft material is dehydrated by air drying or vacuum drying, sterilized with ethylene oxide, and stored in a hermetically sealed enclosure at room temperature until needed, having an indefinite storage life. When needed, the tissue graft material is rehydrated, cut to match the size of the wound, and applied to the wound. The graft may be overlaid with nylon mesh, or bandaged with an elastic tubular dressing.

Previously, the tunica serosa had simply been discarded from xenograft tissues. The present inventor has found, however, that the tunica serosa from the small intestine adheres almost instantaneously to the wound area, remains for a long period without shrinkage or distortion, and when stored as described above, has a long or indefinite storage life. The tissue graft material is particularly well suited for superficial and deep second degree burns (partial thickness burns, erosions, or abrasion by cosmetic peeling).

The tunica serosa is a membrane lining the external walls of the body cavities and is reflected over the surfaces of protruding organs, i.e., the tunica serosa is the membrane lining body cavities. Reference is made to the sole drawing FIGURE in U.S. Pat. No. 4,902,508, issued Feb. 2, 1990 to Badylak et al., the drawing FIGURE being hereby incorporated by reference, in which the tunica serosa is shown as layer B. In preparing tissue for conventional xenografts, this layer is discarded.

In the present invention, however, it is the tunica serosa that is used for tissue grafting, and the remaining layers are discarded. The tissue is obtained from the small intestine of a warm-blooded vertebrate, typically porcine, bovine, ovine, canine, caprine, equine, or piscine tissue, but not excluding other species. Such animals may be destroyed at a slaughterhouse, a rendering plant, a veterinary clinic, or some other location. At that time, the small intestine, or a portion of the small intestine to be used to obtain tissue graft material, is removed and stored in isotonic saline in a hermetically sealed enclosure.

The small intestine, or portion thereof, may then be further processed at a clinic, laboratory, hospital, or other sterile or sanitary facility. The portion of the small intestine is removed from the hermetically sealed enclosure. Using aseptic techniques, the dried tissue is then passed through three (3) rinses of isotonic saline solution for fifteen (15) minutes, one (1) rinse of 0.02% sodium hypochlorite, and a final rinse of saline solution to remove residual chemicals.

After rinsing, the tissue is subjected to treatment with hydrogen peroxide (about 2% concentration by volume) for about one-half hour to ensure the absence of contaminants, e.g., endotoxins, pyrogens, and the like. The tunica serosa is then removed from the small intestine. One method for obtaining the tissue is everting the intestine, incising the tubular material longitudinally, and delaminating the tunica serosa from the remaining tissue by gentle abrasion using moistened gauze in order to remove the tunica muscularis, tunica submucosa, and tunica mucosa of the intestinal tissue. However, other methods may be used for delaminating the tunica serosa from the underlying mucosal and submucosal layers, such as by using a disinfected or sterile casing machine.

Once removed from the other layers of intestinal tissue, the tunica serosa is cut into pieces having a length of about eight inches. Preferably, the tunica serosa is then perforated by discrete punctures. The purpose of perforating the tissue graft material is to permit wound exudates to escape through the perforations once the graft is in place, rather than allowing the exudates to build up under the membrane. The tunica serosa may then be dehydrated by air-drying or vacuum drying.

The tissue graft material is then re-sterilized with ethylene oxide and stored in a hermetically sealed enclosure at room temperature. Tunica serosa prepared and stored in this manner has a long or indefinite storage life.

When needed for use as a tissue graft, the tunica serosa is rehydrated. The surface area requiring the skin graft is treated with an antiseptic to produce a cleansed graft zone. The tissue graft is cut into a planar shape having a size substantially corresponding to the cleansed graft zone. The tissue graft is then layered onto the cleansed graft zone to produce a dressed graft zone. The tissue graft adheres to the exposed wound surface area almost instantaneously, and may remain for long periods without shrinkage and without distortion. The dressed wound may be covered with a nylon mesh or an elastic, tubular bandage. The wound and the tissue may alternatively be exposed to light for desiccation.

The tunica serosa may be used for tissue grafts to humans, but may also be used for veterinary purposes for skin grafts to horses, dogs, or other vertebrates in need of closure of wounds resulting from burns, cuts, or other causes.

It is to be understood that the present invention is not limited to the embodiments described above, but encompasses any and all embodiments within the scope of the following claims.

I claim:

1. A tissue grafting method for treating wounds on a surface area, comprising the steps of:
    treating a surface area requiring a skin graft with an antiseptic to produce a cleansed graft zone;
    cutting a tissue graft consisting of the tunica serosa from the small intestine of porcine tissue into a planar shape having a size substantially corresponding to the cleansed graft zone; and
    layering the porcine tissue graft onto the cleansed graft zone to produce a dressed graft zone.

2. The tissue grafting method according to claim 1, further comprising the step of rehydrating the tissue graft prior to the step of cutting the tissue graft if the tissue graft has been stored in a dehydrated state.

3. The tissue grafting method according to claim 1, further comprising the step of covering the dressed graft zone with nylon mesh.

4. The tissue grafting method according to claim 1, further comprising the step of covering the dressed graft zone with an elastic, tubular bandage.

5. The tissue grafting method according to claim 1, further comprising the step of exposing the dressed graft zone to light for desiccation.

6. The tissue grafting method according to claim 1, wherein said step of treating a surface area requiring a skin graft further comprises treating a surface area of a human being requiring a skin graft.

7. The tissue grafting method according to claim 1, wherein said step of treating a surface area requiring a skin graft further comprises treating a surface area of a vertebrate requiring a skin graft.

8. The tissue grafting method according to claim 1, wherein the porcine tissue graft has a plurality of perforations formed therein for permitting wound exudates to escape through the perforations.

* * * * *